US00PP23187P2

(12) United States Plant Patent
van Haaster

(10) Patent No.: US PP23,187 P2
(45) Date of Patent: Nov. 13, 2012

(54) ***DAHLIA* PLANT NAMED 'FIDAHHYPPURBICO'**

(50) Latin Name: *Dahlia variabilis*
Varietal Denomination: Fidahhyppurbico

(75) Inventor: Johanna G. H. van Haaster, Hillegom (NL)

(73) Assignee: Fides B.V., De Lier (NL)

( * ) Notice: Subject to any disclaimer, the term of this patent is extended or adjusted under 35 U.S.C. 154(b) by 69 days.

(21) Appl. No.: 12/931,170

(22) Filed: Jan. 26, 2011

(51) Int. Cl.
*A01H 5/00* (2006.01)

(52) U.S. Cl. ..... Plt./321

(58) Field of Classification Search ..... Plt./321
See application file for complete search history.

*Primary Examiner* — June Hwu
(74) *Attorney, Agent, or Firm* — C. A. Whealy

(57) ABSTRACT

A new and distinct cultivar of *Dahlia* plant named 'Fidahhyppurbico', characterized by its upright, somewhat outwardly spreading and mounding plant habit; early and freely flowering habit; large inflorescences with light purple-colored ray florets; and good postproduction longevity.

1 Drawing Sheet

Botanical designation: *Dahlia variabilis.*
Cultivar denomination: 'FIDAHHYPPURBICO'.

BACKGROUND OF THE INVENTION

The present invention relates to a new and distinct cultivar of *Dahlia* plant, botanically known as *Dahlia variabilis* and hereinafter referred to by the name 'Fidahhyppurbico'.

The new *Dahlia* plant is a product of a planned breeding program conducted by the Inventor in Hillegom, The Netherlands. The objective of the breeding program is to create new pot-type *Dahlia* plants that have a freely branching and flowering habit, attractive ray floret coloration and good postproduction longevity.

The new *Dahlia* plant originated from an open-pollination in Hillegom, The Netherlands of an unnamed selection of *Dahlia variabilis*, not patented, as the female, or seed, parent with an unknown selection of *Dahlia variabilis* as the male, or pollen, parent. The new *Dahlia* plant was discovered and selected by the Inventor as a single flowering plant from within the progeny of the stated open-pollination in a controlled environment in Hillegom, The Netherlands.

Asexual reproduction of the new *Dahlia* plant by cuttings in a controlled environment in Hillegom, The Netherlands since 2008 has shown that the unique features of this new *Dahlia* plant are stable and reproduced true to type in successive generations.

SUMMARY OF THE INVENTION

Plants of the new *Dahlia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Fidahhyppurbico'. These characteristics in combination distinguish 'Fidahhyppurbico' as a new and distinct cultivar of *Dahlia* plant:

1. Upright, somewhat outwardly spreading and mounding plant habit.

2. Early and freely flowering habit.
3. Large inflorescences with light purple-colored ray florets.
4. Good postproduction longevity.

Compared to plants of the female parent selection, plants of the new *Dahlia* differ primarily in ray floret coloration and plant shape.

Plants of the new *Dahlia* can be compared to plants of *Dahlia* 'Fidahhyppi', disclosed in U.S. Plant Pat. No. 21,254. In side-by-side comparisons conducted in De Lier, The Netherlands, plants of the new *Dahlia* differed primarily from plants of 'Fidahhyppi' in ray floret color as plants of 'Fidahhyppi' had red purple-colored ray florets.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant. The photograph comprises a side perspective view of a typical flowering plant of 'Fidahhyppurbico' grown in a container.

DETAILED BOTANICAL DESCRIPTION

The aforementioned photograph and the following observations and measurements describe plants grown during the autumn in 15-cm containers in a glass-covered greenhouse in De Lier, The Netherlands and under conditions and practices which approximate those generally used in commercial potted *Dahlia* production. During the production of the plants, day and night temperatures averaged 18° C. Plants were nine weeks old when the photograph and description were taken. In the following description, color references are made to The Royal Horticultural Society Colour Chart, 2007 Edition, except where general terms of ordinary dictionary significance are used.

Botanical classification: *Dahlia variabilis* 'Fidahhyppurbico'.

Parentage:

*Female, or seed, parent*.—Unnamed selection of *Dahlia variabilis*, not patented.

*Male, or pollen, parent*.—Unknown selection of *Dahlia variabilis*, not patented.

Propagation:

*Type*.—By cuttings.

*Time to initiate roots, summer*.—About six days at temperatures of about 22° C.

*Time to initiate roots, winter*.—About eight days at temperatures of about 20° C.

*Time to produce a rooted young plant, summer*.—About 12 days at temperatures of about 22° C.

*Time to produce a rooted young plant, winter*.—About 16 days at temperatures of about 20° C.

*Root description*.—Fine, fibrous; tuber development has not been observed.

*Rooting habit*.—Freely branching; dense.

Plant description:

*Plant form and growth habit*.—Upright, somewhat outwardly spreading and mounding plant form; broad inverted triangle; three primary lateral branches develop, each primary lateral branch with numerous secondary branches; inflorescences held above the foliar plane on strong peduncles; bushy and dense habit; moderately vigorous growth habit.

*Plant height*.—About 27 cm.

*Plant diameter or spread*.—About 30 cm.

*Lateral branches*.—Length: About 20 cm. Diameter: About 7 mm. Internode length: About 1.5 cm to 2 cm. Aspect: Erect to somewhat outwardly spreading. Strength: Moderately strong. Texture: Smooth, glabrous. Color: Close to 144B.

Foliage description:

*Arrangement*.—Leaves opposite; leaves may be simple or compound with three or five leaflets; measurements are for simple leaves.

*Shape*.—Ovate.

*Apex*.—Acute.

*Base*.—Attenuate.

*Margin*.—Serrate to dentate.

*Length*.—About 10 cm.

*Width*.—About 6.5 cm.

*Venation pattern*.—Pinnate.

*Texture, upper and lower surfaces*.—Slightly pubescent; slightly rough.

*Color*.—Developing leaves, upper surface: Close to 137B. Developing leaves, lower surface: Close to 138B. Fully expanded leaves, upper surface: Close to N137A; venation, close to N137A. Fully expanded leaves, lower surface: Close to 138B; venation, close to 138A.

*Petioles*.—Length: About 4.2 cm. Diameter: About 3 mm. Texture, upper and lower surfaces: Smooth, glabrous. Color, upper and lower surfaces: Close to 144B.

Inflorescence description:

*Appearance and arrangement*.—Rotate double inflorescence form with ray florets forming acropetally on a receptacle; inflorescences positioned above the foliar plane on strong peduncles; inflorescences face upright to outwardly; freely flowering habit, about 20 inflorescences develop per plant.

*Fragrance*.—None detected.

*Time to flower*.—Plants flower continuously from spring through the autumn in The Netherlands; early flowering habit, plants begin flowering about seven to eight weeks after planting.

*Post-production longevity*.—Inflorescences maintain good substance for about two weeks on the plant; inflorescences persistent.

*Inflorescence bud*.—Height: About 4 mm. Diameter: About 6 mm. Shape: Globular, flattened. Color: Close to N144A.

*Inflorescence size*.—Diameter: About 9 cm. Depth (height): About 4 cm. Disc diameter: About 5 mm. Receptacle height: About 3 mm. Receptacle diameter: About 2 cm.

*Ray florets*.—Quantity per inflorescence: About 118 arranged in about nine whorls. Length: About 3.6 cm. Width: About 2 cm. Shape: Oblanceolate. Apex: Acute, cuspidate or emarginate. Base: Cuneate. Margin: Entire. Aspect: Initially upright to eventually roughly perpendicular to the peduncle; ray florets cupped. Texture, upper and lower surfaces: Smooth, glabrous. Color: When opening and fully opened, upper surface: Towards the apex, close to 75A; mid-section, close to 75A to 75C; towards the base, close to 6A; longitudinal stripe, close to 72A. When opening and fully opened, lower surface: Close to 72A slightly tinted with close to 75A.

*Disc florets*.—Length: About 8 mm. Diameter: About 1 mm. Shape: Tubular, elongated; apices obtuse. Number of disc florets per inflorescence: About 24. Color, when opening and fully opened: Apex: Close to 6A. Mid-section: Close to 17A. Base: Close to 145D.

*Phyllaries*.—Quantity per inflorescence: About seven to eight arranged in a single whorl. Length: About 1.1 cm. Width: About 6 mm. Shape: Ovate. Apex: Acute. Base: Cuneate. Margin: Entire. Texture, upper and lower surfaces: Smooth, glabrous. Color, upper surface: Close to 137C. Color, lower surface: Close to 138A.

*Peduncles*.—Length: About 12 cm. Diameter: About 3 mm. Aspect: Mostly erect. Strength: Strong. Texture: Smooth, glabrous. Color: Close to 144A tinted with close to 183B.

*Reproductive organs*.—Androecium: Quantity per floret: About two. Filament length: About 8 mm. Filament color: Close to 14A. Anther shape: Narrowly elliptic. Anther length: About 2 mm. Anther color: Close to 14A. Pollen amount: Moderate. Pollen color: Close to 17A. Gynoecium: Not observed. Seeds/fruits: Seed and fruit development have not been observed.

Disease/pest resistance: Plants of the new *Dahlia* have not been shown to be resistant to pathogens and pests common to *Dahlia*.

Temperature tolerance: Plants of the new *Dahlia* tolerate high temperatures of about 35° C. and are hardy to USDA Hardiness Zone 8.

It is claimed:

1. A new and distinct *Dahlia* plant named 'Fidahhyppurbico' as illustrated and described.

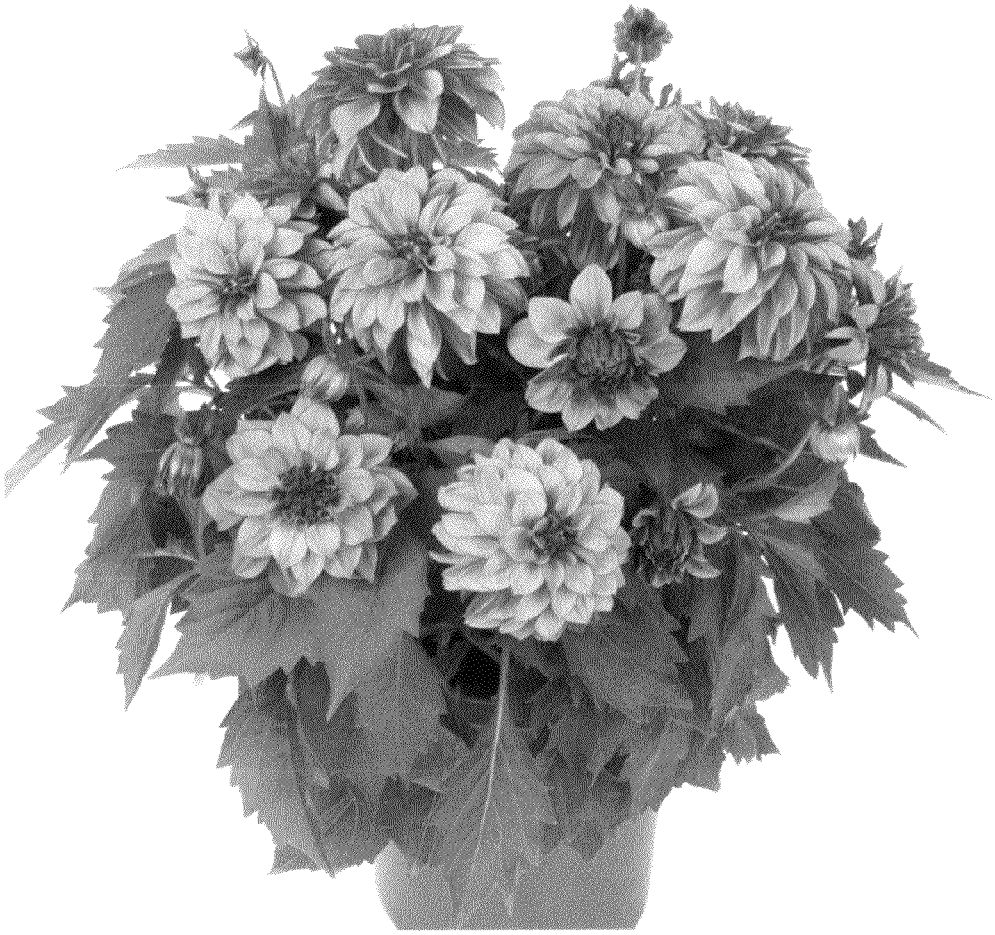

* * * * *